US006661876B2

United States Patent
Turner et al.

(10) Patent No.: US 6,661,876 B2
(45) Date of Patent: Dec. 9, 2003

(54) MOBILE MINIATURE X-RAY SOURCE

(75) Inventors: Clark Turner, Payson, UT (US); Arturo Reyes, Orem, UT (US); Hans K. Pew, Acton, MA (US); Mark W. Lund, Orem, UT (US); Michael Lines, Provo, UT (US); Paul Moody, Sandy, UT (US); Sergei Voronov, Provo, UT (US)

(73) Assignee: Moxtek, Inc., Orem, UT (US)

( * ) Notice: Subject to any disclaimer, the term of this patent is extended or adjusted under 35 U.S.C. 154(b) by 44 days.

(21) Appl. No.: 10/208,646

(22) Filed: Jul. 29, 2002

(65) Prior Publication Data

US 2003/0021377 A1 Jan. 30, 2003

Related U.S. Application Data

(60) Provisional application No. 60/308,637, filed on Jul. 30, 2001.

(51) Int. Cl.$^7$ ................................................ H01J 35/14
(52) U.S. Cl. ...................... 378/138; 378/119; 378/102; 378/123; 313/553
(58) Field of Search .......................... 378/119, 122, 378/123, 138, 143, 101, 102, 64, 65; 313/553

(56) References Cited

U.S. PATENT DOCUMENTS

| | | | |
|---|---|---|---|
| 4,463,338 A | 7/1984 | Utner et al. ................. 338/281 |
| 5,010,562 A | 4/1991 | Hernandez et al. .......... 378/125 |
| 5,117,829 A | 6/1992 | Miller et al. .................... 378/4 |
| RE34,421 E * | 10/1993 | Parker et al. ................. 378/121 |
| 5,400,385 A | 3/1995 | Blake et al. .................. 378/112 |
| 5,428,658 A | 6/1995 | Oettinger et al. |
| RE35,383 E | 11/1996 | Miller et al. |
| 5,621,780 A | 4/1997 | Smith et al. |
| 5,729,583 A | 3/1998 | Tang et al. .................. 378/122 |
| 6,044,130 A | 3/2000 | Inazura et al. .............. 378/138 |
| 6,075,839 A | 6/2000 | Treseder ..................... 378/140 |
| 6,134,300 A | 10/2000 | Trebes et al. ................ 378/136 |
| 6,351,520 B1 * | 2/2002 | Inazaru ........................ 378/138 |
| 6,477,235 B2 * | 11/2002 | Chornenky et al. ......... 378/143 |
| 6,546,077 B2 * | 4/2003 | Chornenky et al. ......... 378/122 |

* cited by examiner

Primary Examiner—Drew A. Dunn

(57) ABSTRACT

A mobile, miniature x-ray source includes a low-power consumption cathode element for mobility, and an anode optic creating a field free region to prolong the life of the cathode element. An electric field is applied to an anode and a cathode that are disposed on opposite sides of an evacuated tube. The anode includes a target material to produce x-rays in response to impact of electrons. The cathode includes a cathode element to produce electrons that are accelerated towards the anode in response to the electric field between the anode and the cathode. The tube can have a length less than approximately 3 inches, and a diameter or width less than approximately 1 inch. The cathode element can include a low-power consumption cathode element with a low power consumption less than approximately 1 watt. The power source can include a battery power source. A field-free region can be positioned at the anode to resist positive ion acceleration back towards the cathode element. An anode tube can be disposed at the anode between the anode and the cathode, and electrically coupled to the anode so that the anode and the anode tube have the same electrical potential, to form the field-free region.

28 Claims, 4 Drawing Sheets

MOBILE MINIATURE X-RAY SOURCE

Priority is claimed of U.S. Provisional Patent Application No. 60/308,637, filed Jul. 30, 2001.

BACKGROUND OF THE INVENTION

1. Field of the Invention

The present invention relates generally to the production of an x-ray beam by electron impact on a metal target. More particularly, the present invention relates to a transmission type x-ray source that is mobile, miniature, with a configuration allowing placement of a sample close to the point where X rays are generated, with a configuration allowing close placement of a detector in XRF application, and with an electron optical element configuration that allows the generation of a small diameter spot as the source of X rays.

2. Related Art

In an X-ray tube, electrons emitted from a cathode source are attracted to an anode by the high bias voltage applied between these two electrodes. The intervening space must be evacuated to avoid electron slowing and scattering, but primarily to prevent ionization of containment gas and acceleration of the resulting ions to the cathode where they erode the filament and limit tube life. Characteristic and Bremsstrahlung X rays are generated by electron impact on the anode target material. Every material is relatively transparent to its own characteristic radiation, so if the target is thin, there may be strong emission from the surface of the target that is opposite the impacted surface. This arrangement is termed a transmission type X-ray tube. By comparison, a side-window tube has a thick anode in the vacuum space; and its X-ray emission passes from the tube via an X-ray transparent window placed in the side of the vacuum chamber. Each type has its advantages and disadvantages, depending upon the intended application.

Typical X-ray tubes are bulky and fragile, and must be energized by heavy, high-voltage power supplies that restrict mobility. Thus, samples must be collected and brought to the X-ray unit for analysis. This is very inconvenient for popular X-ray applications. Certain "field applications" include X-ray fluorescence (XRF) of soil, water, metals, ores, well bores, etc., as well as diffraction and plating thickness measurements.

A popular approach to portability of low power X-ray sources is the use of $^{109}$Cd which emits silver K X-ray lines during radioactive decomposition. There are many such instrumental sources currently in use, and software has been developed to make XRF with the silver line sensitive and reliable. Unfortunately the intensity of emission from $^{109}$Cd decays exponentially with a half-life of about 1.2 years. This necessitates frequent recalibration and eventual disposal of the $^{109}$Cd. The size of such radioactive sources are 1 or 2 Curies, so a license is required for transportation and possession of this isotope in the quantities useful for XRF.

Miniature size X-ray tubes have been demonstrated for medical purposes. For example, see U.S. Pat. Nos. 5,729, 583 and 6,134,300. The geometry, however, is wrong for analysis. Such tubes are designed to send X rays into at least π steradians for therapeutic reasons, rather than concentrating radiation in a spot that is easily accessed by a detector. Thus, such therapeutic X-ray tubes are inadequate for XRF work in the field because of the divergent beams. Another type of medical tube is a combination device where the X rays are for diagnostic purposes, i.e. tube placed in the body internally. Emitted X rays pass through tissue to film that is external to the body. This reveals the position of tumors or anatomic maladies. For example, see U.S. Pat. Nos. 5,010, 562 and 5,117,829. With respect to the '562 patent, it is important to note that the foil is not a transmission type anode, but an electron window. With respect to the '829 patent, an interesting nozzle is shown, but the rest of the apparatus is large and inadequate for mobile field work.

Another type of x-ray tube includes a rod anode used for insertion into pipes and boilers for X-ray inspection. The metal anode rod is hollow from the point the electron beam enters to its opposite end, which is the target for the production of X rays. The whole rod structure is at the anode potential. A window in the side of the rod allows X rays to be emitted from the anode. To focus the electron beam on the target at the end, a magnetic coil is positioned along the rod. This electromagnet is heavy and requires considerable power from a large battery if it is to be portable. What is more, a long anode is of little value in typical analytical applications. Such rod-anode tubes are not of the transmission type.

To obtain a source of X rays that is of small diameter at the anode target of an X-ray tube, electrodes or apertures or both have been used in the tube. These are designed to focus the electron beam to a small spot on the target. One of these electrodes is termed a Wehnelt aperture. It is near the cathode, as is done in electron guns for microscopes. This seriously limits the electron flux. It is more important to limit the diameter of the electron beam where it strikes the anode, since this is the proximal source of X rays intended to strike a small portion of the analyte. This typically requires other electrodes. One type is a focusing electrode extending from the cathode region to approximately half way to the anode. This typically cylindrical tube reduces the distance between points of high and low voltage and it can lead to electrical breakdown in the tube.

An important feature of an X-ray tube used to excite X-ray fluorescence for elemental analysis is that the point where the X rays are generated be as close as possible to the sample being irradiated. This is necessary because the intensity of the X rays drops off in proportion to the reciprocal of the square of the distance from the target spot. It is a further advantage if the X-ray flux is focused to a small spot on the sample for reasons of spatial resolution, which allows analysis of discrete, small portions of a complex sample. In XRF, this X-ray beam is used to excite elements in the sample. They, in turn, fluoresce characteristic radiation in a Lambertian pattern, so XRF sensitivity is maximized if there is an angle of about 45° between the beam illuminating the analyte and the fluoresced X rays going to the detector. For generic X-ray tubes, the spot impacted by electrons is broad and blunt, so the detector must be placed to one side with an angle that is 90° or more instead of the desired 45°.

An object of the Treseder patent (U.S. Pat. No. 6,075,839) is to make the target accessible to the sample, but the exit window end of this invention is necessarily broadened (greater than 20 mm). In addition, the anode is seriously recessed from the window because the tube's electron gun is placed at the side of the anode instead of generally behind it. What is more, it is impossible to modify the Treseder design because the target must be well separated from the X-ray window to make room for the curvature of the electron beam. The result is a large distance between the target and the sample, as shown in FIG. 3 of that patent.

Another requirement for sensitive XRF is irradiation with the correct band of wavelengths for exciting the sample. Higher bias voltage not only increases X-ray flux, but it changes the spectrum of the output. The bias should be subject to selection by the operator, and this setting should be independent of the tube current setting. In general, the higher the X-ray flux (and corresponding tube current), the more sensitive and accurate will be the measurements, whether they are XRF, plating thickness, or diffraction. However, once the detector is saturated, additional power is of no use. The current of the electron beam should be adjusted to produce adequate but not excessive x-ray intensity.

For generic X-ray tubes, substantial cooling is required because upon electron impact, and less than 1% of the electron beam power is converted to X-ray power. The rest of the energy becomes heat in the target. Heat also arises from thermionic electron sources. The heat cannot be allowed to accumulate and raise the temperature of the tube because high temperature decreases the lifetime of several tube parts. Thermal shock is especially destructive. Therefore, when operating at sufficient power, most X-ray tubes need to be cooled with a flowing liquid or forced air. The cooling effectiveness is limited primarily by the slow conduction of thermal energy through thick portions of the tube (e.g. the anode, in particular). Miniaturization reduces this problem to some extent, but cooling is still required for the inventions of U.S. Pat. No. 6,075,839 (cooling by oil, $SF_6$, or forced air) and U.S. Pat. No. 6,044,130 which has exterior protrusions to aid in cooling by forced air. To obtain sufficient X-ray flux, all of the currently available X-ray tubes must be so large that they must be cooled. That is, a sufficiently powerful tube that is cooled only by ambient air is currently unavailable.

Another important feature is stability of the X-ray flux over the period of time required to calibrate the tube and measure the samples. This stability should be of the order of ±0.1%. Typical small high-voltage DC power supplies do not meet this criterion, and the resistivity of the tube can change over short periods of time. Thus, high-voltage stability presents a problem for mobile X-ray tubes.

Although X-ray tubes were first constructed over 100 years ago, no mobile X-ray tube is available for mobile applications such as those addressed by [109]Cd radioactive sources. This is surprising because so many types of X-ray instruments are in use in science and industry. There is clearly a long-felt need for mobile, electronic, X-ray tubes and instrumentation.

SUMMARY OF THE INVENTION

It has been recognized that it would be advantageous to develop a mobile, miniature x-ray source. In addition, it has been recognized that it would be advantageous to develop an x-ray source for field applications. In addition, it has been recognized that it would be advantageous to develop a low-power consumption x-ray source. In addition, it has been recognized that it would be advantageous to develop an x-ray source that is not radioactive. It has also been recognized that it would be advantageous to develop an x-ray source with improved life or durability.

The invention provides a mobile, miniature x-ray source with a low-power consumption cathode element for mobility, and/or an anode optic creating a field free region to prolong the life of the cathode element. The x-ray source includes an evacuated tube. An anode is disposed in the tube and includes a material to produce x-rays in response to impact of electrons. A cathode is disposed in the tube opposing the anode. An electric field is applied to the anode and cathode. The cathode includes a cathode element to produce electrons that are accelerated towards the anode in response to the electric field between the anode and the cathode. A power source is electrically coupled to the anode, the cathode, and the cathode element. The power source provides power for the cathode element, and provides the electric field between the anode and the cathode.

In accordance with a more detailed aspect of the present invention, the tube is configured to be both miniature and mobile. The tube can have a length less than approximately 3 inches, and a diameter or width less than approximately 1 inch. The cathode element can include a low-power consumption cathode element with a low power consumption less than approximately 1 watt. The power source can include a battery power source.

In accordance with another more detailed aspect of the present invention, the battery power source provides an electric field between the anode and the cathode of at least approximately 15 kilo-volts.

In accordance with another more detailed aspect of the present invention, a window can be disposed in the evacuated tube at the anode. The window can be aligned with a longitudinal axis of the evacuated tube to release x-rays substantially along the longitudinal axis. Alternatively, the window can be disposed in a side of the evacuated tube to release x-rays transverse to the longitudinal axis.

In accordance with another more detailed aspect of the present invention, a field-free region can be positioned at the anode to resist positive ion acceleration back towards the cathode element. The electrons can impact the anode and heat the anode, releasing residual gas molecules. In addition, the electrons can ionize the residual gas molecules to positive ions. Such ions would normally be accelerated back to the cathode and sputter-erode the cathode element.

In accordance with another more detailed aspect of the present invention, an anode tube can be disposed at the anode between the anode and the cathode, and electrically coupled to the anode so that the anode and the anode tube have the same electrical potential. The anode tube can create the field-free region.

In accordance with another more detailed aspect of the present invention, a cathode optic can be disposed proximate the cathode element. The cathode optic can including a plate with an aperture therein configured to allow electrons to pass through the aperture towards the anode.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 5b is an exploded view of the field emitter of FIG. 5a; and

DETAILED DESCRIPTION

Figure 1:
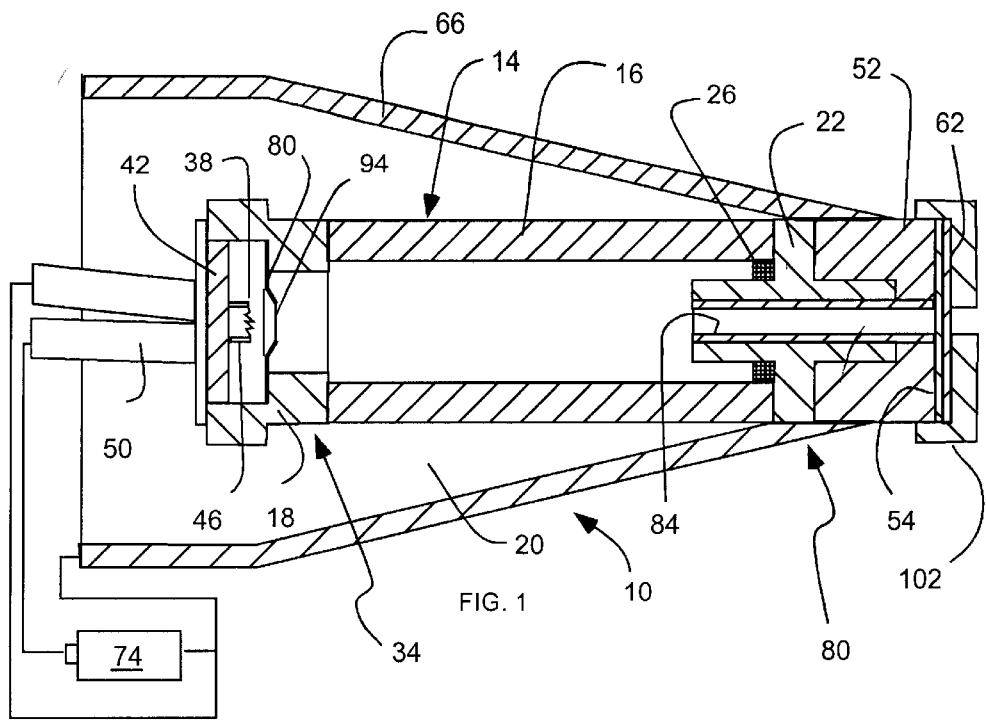
FIG. 1 is a cross-sectional side view of a mobile, miniature x-ray source in accordance with an embodiment of the present invention.
Figure 1B:
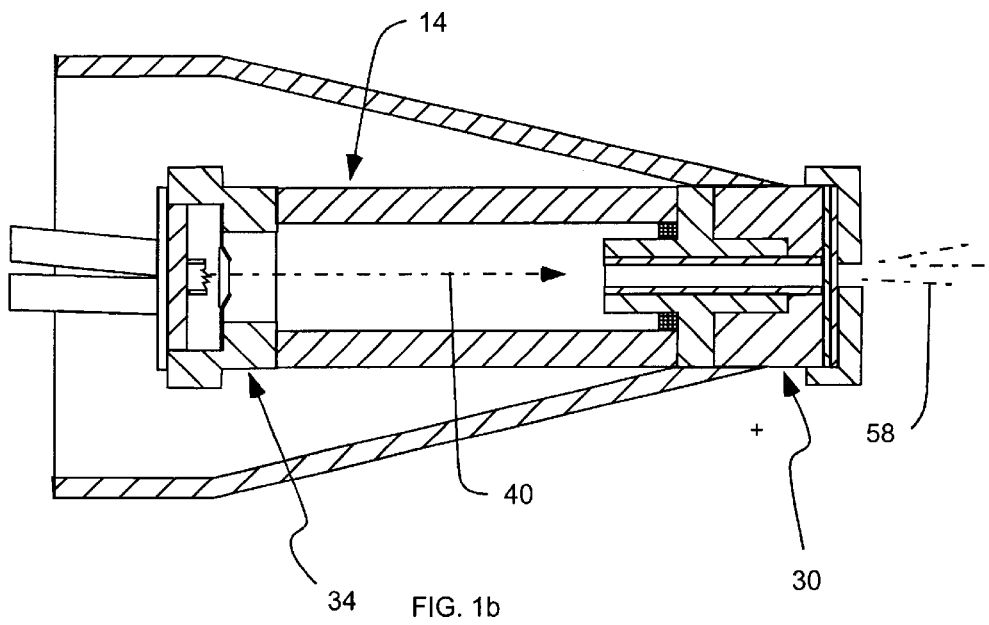
FIG. 1b is a cross-sectional schematic view of the x-ray source of FIG. 1.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 2:
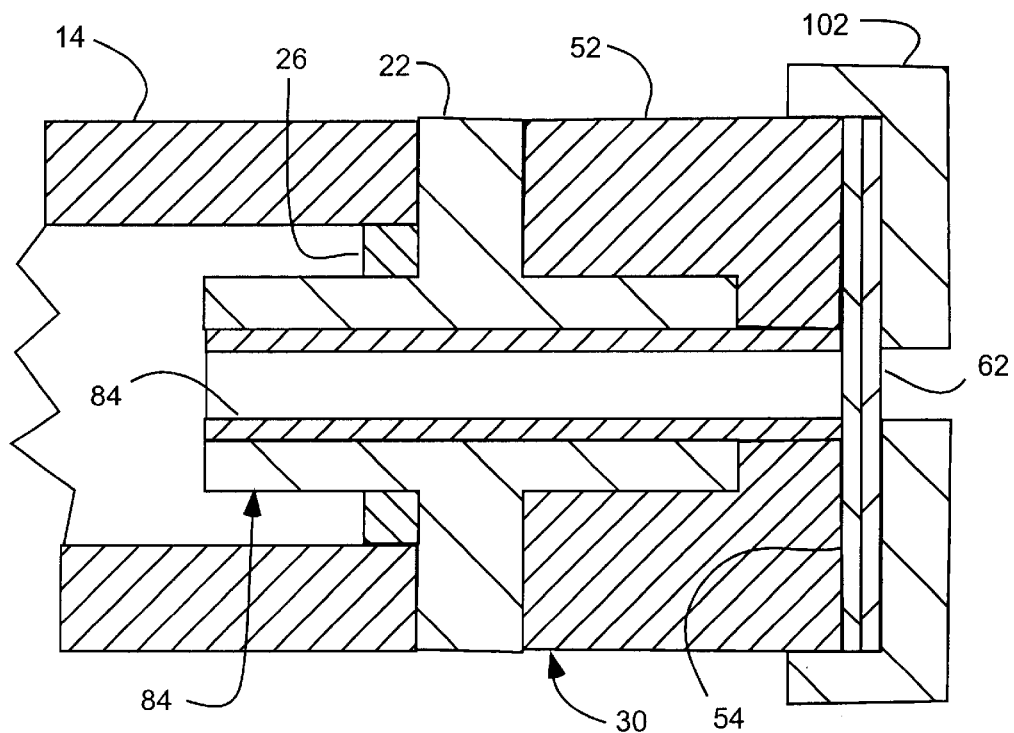
FIG. 2 is a partial cross-sectional side view of the x-ray source of FIG. 1.
Figure 3:
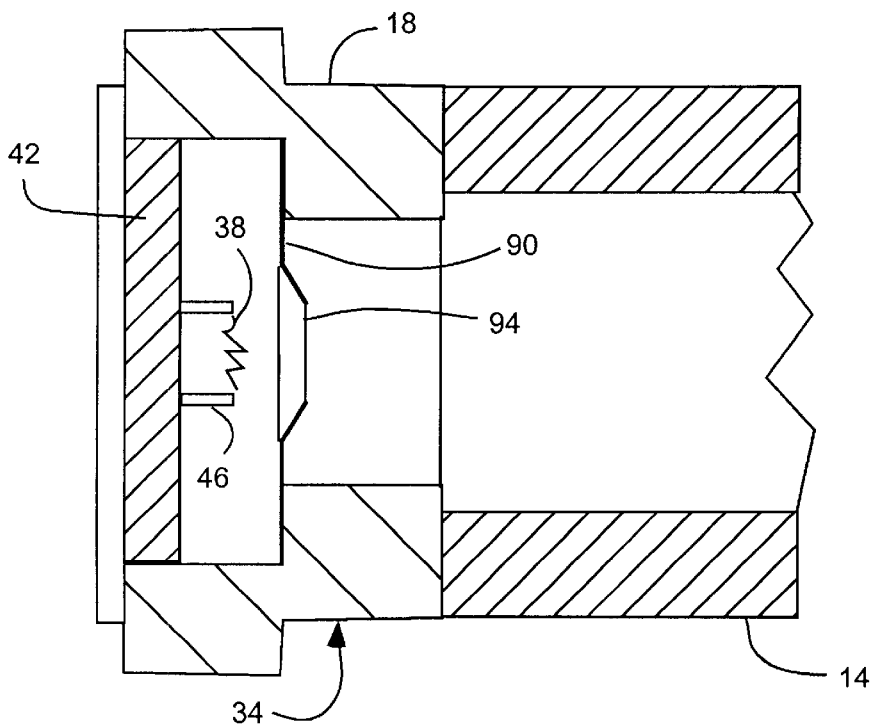
FIG. 3 is a partial cross-sectional side view of the x-ray source of FIG. 1.

As illustrated in FIGS. 1–3, a mobile, miniature x-ray source, indicated generally at 10, in accordance with the present invention is shown. The x-ray source 10 advantageously includes a low power consumption cathode element suitable for use with a battery power source to allow the x-ray source to be mobile for field applications. In addition, the x-ray source 10 advantageously includes an anode optic to create a field-free region at the anode for resisting positive ion acceleration back towards the cathode element, to resist sputter-erosion of the cathode element and to increase the life of the cathode element. "Field applications", such as X-ray fluorescence (XRF) of soil, water, metals, ores, well bores, etc., as well as diffraction and plating thickness measurements, are fields that can benefit from such an x-ray source 10.

The x-ray source 10 includes an evacuated tube or bulb 14. The x-ray source 10 can be a transmission-type x-ray source, and the tube 14 can be a transmission type x-ray tube, as shown. The tube 14 can include an elongated cylinder 16, and in one aspect is formed of a ceramic material, such as aluminum oxide. Ceramic is believed to be superior to the traditionally used glass because of its dimensional stability and its ability to withstand higher voltages. To remove embedded gas, the ceramic is pre-treated by vacuum heating. Extensions 18 and 22 can be attached at opposite ends of the tube 14. The extensions 18 and 22 can be formed of a metal material and brazed to the ceramic tube 14.

A getter 26 or getter material is disposed in the tube 14, and can be attached to the extension 22 to remove residual gasses in the tube after vacuum sealing. The getter 26 can be positioned in a field free position or region, as described in greater detail below. If high cleanliness standards are maintained and evacuation is performed properly, a getter may be unnecessary for tubes with thermionic emitters. The getter can be formed of ST 122/NCF, a Ti/Zr/V/Fe alloy. It can be activated by heating for a period of up to 24 hours.

As stated above, the x-ray source 10 advantageously is mobile and suited for field applications. The x-ray tube or bulb 14 advantageously has a length less than approximately 3 inches, and a diameter or width less than approximately 1 inch, to facilitate mobility and use in field applications.

An anode, indicated generally at 30, and a cathode, indicated generally at 34, are disposed in and/or form part of the tube 14. The anode 30 and cathode 34 are disposed at opposite sides of the tube 14 opposing one another. An electric field is applied between the anode 30 and cathode 34. The anode 30 can be grounded, as described below, while the cathode 30 can have a voltage applied thereto. The cathode can be held at a negative high voltage relative to the anode. Alternatively, the anode can be held at a positive high voltage, while the cathode is grounded.

As stated above, the cathode advantageously is a low power consumption cathode and includes a low-mass, low-power consumption cathode element or filament 38. The cathode element 38 can be a thermionic emitter, such as a miniature coiled tungsten filament. The cathode element 38 produces electrons (indicated at 40 in FIG. 2) that are accelerated towards the anode 30 in response to the electric field between the anode 30 and the cathode 34. The cathode element advantageously has a low power consumption that is intended herein to have a power consumption less than approximately 1 watt. The lower power consumption of the cathode element 38 allows the x-ray source 10 to be battery powered, and thus mobile. In addition, the cathode element advantageously has a low-mass less than approximately 100 micrograms.

A header or end cap 42 can be attached to the extension 18 to support the cathode element 38. Pins or posts 46 can extend through the header or end cap 42, and can support the cathode element 38 therebetween. High voltage wires 50 can be electrically coupled to the pins 46, and thus the cathode element.

A potential of approximately 1 volt across the filament drives a current of about 200 mA, which raises the temperature to about 2300 C. This temperature is cool compared to most thermionic sources, but it provides sufficient electron emission for the intended applications of the x-ray tube. For example, only 20 $\mu$A are required to generate sufficient fluorescence from an alloy to saturate a semiconductor detector. Even higher emission efficiency is obtained if the tungsten cathode is coated with mixed oxides of alkaline earths (e.g. Cs, Ca, or Ba). They do, however, allow operation at temperatures as low as 1000 K. Such coated cathodes can still have a low mass as described above.

There are numerous advantages to this cool, coiled tungsten emitter compared to the conventional hot hairpin type. The cooler wire does not add as much heat, and this eliminates the need for an inconvenient cooling mechanism. The lower temperature reduces tungsten evaporation, so tungsten is not deposited on the anode, and the wire does not become thin and break. The cool tungsten coil, however, does not fall below the Langmuir limit, so space charge can accumulate between it and the Wehnelt optic or cathode optic, described below.

An end piece 52 can be disposed on the extension 22 at the anode 30. The end piece 52 can form a window support structure. The extension 22 can be formed from kover while the end piece 52 can be formed of monel. A bore can be formed through the extension 22 and the end piece 52 through which the electrons 40 pass.

A window or target 54 is disposed at the anode 30 of the end piece 52 to produce x-rays (indicated at 58 in FIG. 2) in response to impact of electrons 40. The window or target 54 can include an x-ray generating material, such as silver. The window or target 54 can be a sheet or layer of material disposed on the end of the anode 30, such as a 2-$\mu$m-thick silver. When electrons 40 form the cathode 34 impact the window or target 54 characteristic silver x-ray emission 58 is largely of the same wavelengths as the popular $^{109}$Cd radioactive x-ray sources.

A filter 62 can be used to remove low-energy Bremsstrahlung radiation. The filter 62 can be disposed at the anode 30 on the target material 54. The filter 62 can include a filter material, such as beryllium. In addition, the filter can be a thin layer or sheet, such as 130 μm of beryllium. The filter 62 or material thereof can coat the window or target 54. With such a configuration, silver L lines may be emitted, but they are absorbed after traveling a very short distance in air. It will be appreciated that additional filtering can be added after or instead of the beryllium. For example, one could use a balanced filter of the type described by U. W. Arndt and B. T. M. Willis in *Single Crystal Diffractometry*, Cambridge University Press, New York, 1966, p. 301.

The various components described above, such as the cylinder 16, the extensions 18 and 22, the end cap 42, the end piece 52, and the window or target 54 form the evacuated tube 14. A shield 66 can be disposed around the tube 14 to provide electrical shielding and shielding from stray x-rays. The shield 66 can be electrically coupled to the anode 30 to provide a ground for the anode. In addition, the shield 66 can be metallic to be conductive and shield x-rays. The shield 66 can be a tubular or frusto-conical shell to allow insulation between the x-ray tube 14 and the shield while contacting the anode 20. A space 70 between the shield 66 and the tube 14 can be potted with a potting compound, such as silicone rubber. In one aspect, the potting material has high thermal conductivity and can include high thermal conductivity materials, such as boron nitride.

The x-ray source 10 also advantageously includes a battery operated, high voltage power supply or battery power source, represented by 74, electrically coupled to the anode 30, the cathode 34, and the cathode element 38. The battery power source 74 provides power for the cathode element 38, and the electric field between the anode 30 and the cathode 34. The battery power source 74 and the low-power consumption cathode element 38 advantageously allow the x-ray source to be mobile for field applications.

In analytical applications, it is important to maintain a constant intensity of the x-ray emission. Therefore, a feature of the power supply is the stability that is maintained by feedback that is proportional to the emission current. Any drift in the resistivity of the tube is quickly neutralized by this means so that the tube current remains constant. The power supply can be similar to that described in U.S. Pat. No. 5,400,385, but in the present invention, the power supply is small and battery powered.

In addition, the x-ray source 10 advantageously includes an anode optic, indicated generally at 80. The anode optic 80 is located in the x-ray tube 14 at the anode 30, and creates a field free region to resist positive ion acceleration back towards the cathode element 38. Although, the x-ray tube 14 is evacuated, and can include a getter 26, the impact of electrons 40 on the window or target 54 can heat the anode 30, causing the release of residual gas molecules. The electrons 40 from the cathode element 38, in addition to impacting the window or target 54 to produce x-rays 58, can also ionize the residual gas from the heated anode 30 to positive ions. Normally, such positive ions would be accelerated back to the cathode 34, and can sputter-erode the cathode element 38. Because the cathode element 38 is a low power consumption element, it can have a low mass. Thus, such sputter-erosion from the positive ions can significantly damage the cathode element, and detrimentally affect the life of the cathode element. The field free region created at the anode by the anode optic 80, however, resists the acceleration of positive ions back towards the cathode element 38, thus resisting sputter erosion of the cathode element, and improving the life of the cathode element and x-ray tube.

The anode optic 80 can include an elongated anode tube 84 disposed at the anode 30 and window or target 54. One end of the elongated anode tube 84 can be in contact, or immediately adjacent to, the window or target 54. The anode optic 80 and tube 84 are at the same electrical potential as the window or target 54 or the anode 30. Thus, the anode tube 84 and anode 30 can be grounded. The field free region can be formed in a hollow of the tube. The tube 84 can be formed of silver, and can have an inner diameter of 1.6-mm. The anode optic 80 operates on the diverging beam of electrons 40 to focus them at the window or target 54. The anode optic 80 can be focused by having the proper distance between its open end and the cathode. Focusing may be necessary to create a small spot where x-rays are emitted, and also to prevent stray electrons from striking the inside of the tube. If any stray electrons strike the inside of the tube, the resulting emission of x-rays is of the same wavelengths as those of the target, which is composed of the same material. The tube 84 should completely cover the extension 22 and the end piece 52. As stated above, the tube 84 should extend or reach all the way to the window or target 54, otherwise a halo of unwanted wavelengths can appear around the x-ray beam.

In one aspect, the anode tube 84 and the anode 30 can include the same material, or can be formed of the same material, to prevent contamination of the output spectrum. For example, the anode 30 and the anode tube 84 can be formed of silver, palladium, tungsten, rhodium, titanium, chromium, etc.

It will be appreciated that the anode optic 80 and the low-power consumption cathode element 38 work together to provide a mobile x-ray source. The lower-power consumption cathode element 38 allows for a battery power source, while the anode optic 80 resists untimely erosion of the low-power consumption cathode.

The x-ray source 10 also can include a cathode optic 90 disposed near the cathode 34. The cathode optic 90 can include a disc disposed between the cathode 34 and anode 30. An aperture 94 can be disposed in the disc and aligned along a path of travel between the cathode element 38 and the window or target 54. An indentation can be formed in the disk and can surround the aperture. The disc can be formed of metal. The cathode optic 90 can be a type of Wehnelt optic, but its shape is the inverse of the reentrant Wehnelt (or IRW). The voltage of the cathode optic 90 can be independently controlled, but is kept at the cathode potential in the current configuration. The cathode optic 90 limits the divergence of the emitted electron stream sufficiently that the anode optic 80 or tube 84 can focus the electrons without the major aberrations present with the fully divergent beam. Although the coiled thermionic emitter is large compared to the hairpin type, the aperture of the cathode optic exposes an area of space charge that can be focused on the anode. In fact, this aperture and the aperture of the anode optic are at different electrical potentials, and they form an electrostatic lens. The electron beam focus at the anode is surprisingly tight. In addition, it is not necessary to center the filament in this configuration because the cathode optic positions the source of electrons with respect to the anode.

Without the anode and cathode optics 80 and 90, the electron beam is weak and diffuse at the target. Only about 30% of the current emitted by the filament actually strikes the window. By contrast, if both the anode and cathode optics are present, more than 60% of the emission current strikes the anode target. What is more, the filament is imaged on the target with close to a 1:1 magnification. The result is emission of x-rays from a spot that has only a 0.3 mm diameter. This is far smaller than the size of typical x-ray sources. In addition, the x-rays are generated within the thin window so the distance between the point where the x-rays arise and the sample can be as short as a few millimeters. In another aspect, a Pierce-type electron gun can replace the cathode optic. The x-ray tube advantageously produces a sub-millimeter spot on the anode from which x-rays are emitted. In addition to being important for micro-XRF applications, a small X-ray source can be necessary for high-resolution imaging and for accurate crystallography.

An x-ray collimator 102 can be disposed on the end of the x-ray tube 14 at the anode 30 to direct x-rays in a desired direction. The collimator 102 can be disposed on the target 54 or filter 62. The collimator 102 includes a bore therethrough aligned with the path from the cathode element 38 to the window or target 54. The collimator 102 intercepts x-rays that exit at angles that are large relative to the window normal. The collimator 102 can be formed of silver to prevent the generation of unwanted x-ray wavelengths. The x-ray collimator 102 can be held at ground potential to avoid the possibility of electric shock to the operator of the device.

With the configuration described above, it has been found that the spectrum of the anode includes silver $K_\alpha$ and $K_\beta$ lines, and surprisingly intense L lines, as well as Bremsstrahlung radiation extending to the acceleration potential and also to the lower limit. This low-energy limit is determined by absorption in the target anode and in the x-ray filter. The spectrum is responsive to the magnitude of the bias voltage. The intensity ratios of the K and L lines can be changed by the thickness of the target anode, which absorbs L lines better than K lines. The spectrum can also be adjusted by changing the material and thickness of the x-ray filter, or by the addition of the previously mentioned balanced filter.

Figure 5A:
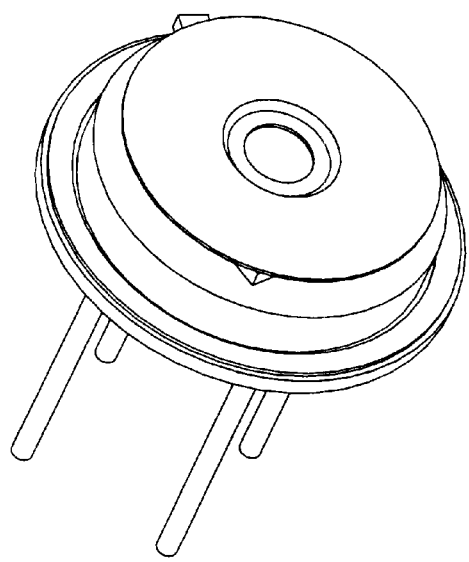
FIG. 5a is a perspective view of a field emitter of a mobile, miniature x-ray source in accordance with an embodiment of the present invention.
Figure 5B:
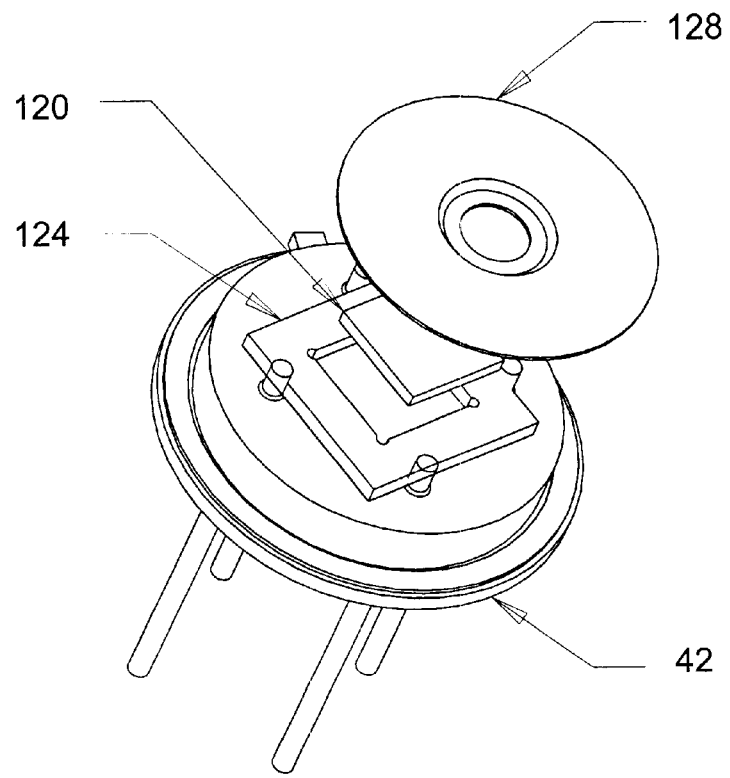

As described above, the cathode element 38 can be a thermionic emitter. Other types of electron emitters also can be used. For example, referring to FIG. 5, a field emitter 120 can be used. The field emitter 120 can include a centering frame 124. The centering frame 124 can be formed of ceramic. The centering frame 124 can be mounted onto the end cap or header 42. A disc 128 can overlay the field emitter 120. The disc 128 can include an aperture to allow transmission of electrons. The disc can be formed of stainless steel. The field emitter tips can be ruined if operated with a back-pressure of more than about $10^{-8}$ mm Hg, so a getter is advisable in the x-ray tube. The cathode portion of the power supply can place about 80 volts on the field emitter gates. In contrast to the thermionic filament, the field emitter draws virtually no current other than that emitted toward the anode, and they do not heat other parts of the tube. What is more, while the high voltage remains on, the gate voltage can be switched or modulated to control electron emission and subsequent x-ray emission at very high frequencies.

As another example of an electron emitter, a ferroelectric solid can be provided to emit electrons. Again, the cathode portion of the power supply can be adapted. In this case, the power supply can provide pulses of higher voltage to the ferroelectric.

Other electron emitters can be used, including metal tip arrays, gate-modulated emitters either in arrays or field emitting surfaces, carbon nanotubes with or without modulating gates, heated lanthanum hexaboride (LaB6), etc.

As described above, the x-ray source 10 is configured to emit x-rays 58 along its longitudinal axis. The cathode element 38 and window or target 54 are aligned along a longitudinal axis of the x-ray tube 14. The anode optic 80 and cathode optic 90 are similarly aligned along the longitudinal axis.

Figure 4:
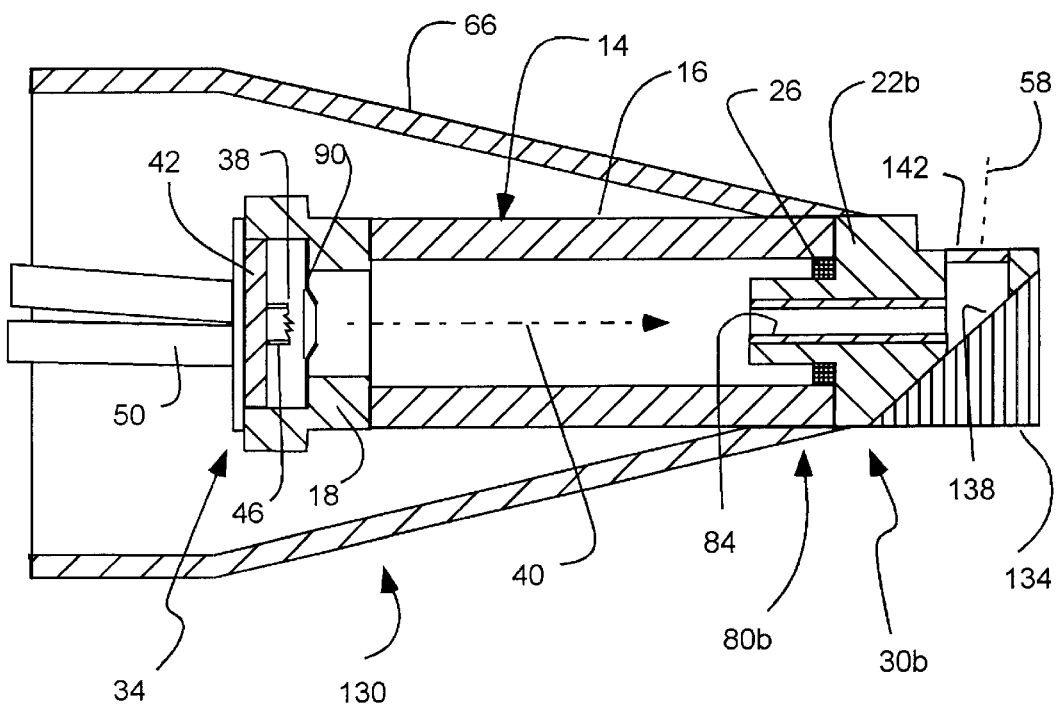
FIG. 4 is a cross-sectional side view of another mobile, miniature x-ray source in accordance with an embodiment of the present invention.

Referring to FIG. 4, another x-ray source 130 is shown that is similar in many respects to the x-ray source described above, but that is configured to emit x-rays 58 transverse to the longitudinal axis, or to emit laterally. The x-ray source 130 can include an anode 30b with a target or target material 134 that includes a more massive block of metal, such as copper for x-ray diffraction applications. Other electrically conductive targets could be used. The target 134 can have an angled surface 138 oriented at an acute or obtuse angle (as opposed to a right angle) with respect to the electron 40 path or longitudinal axis of the x-ray tube 14. The angled surface 138 directs x-rays 58 laterally or transverse to the longitudinal axis. A window 142 can be form in or disposed at the anode 30b, and positioned on a lateral side of the anode adjacent the angled surface 138 so that x-rays from the target pass through the window. The window can be formed of a material including beryllium. The window can be made of other materials, and it can be covered with a filter material, such as nickel that can provide a β filter for copper emissions.

The x-ray source 130 also can have an anode optic 80b to create a field free region as described above. The anode optic 80b can include an axial hole formed through the extension 22b and/or end piece.

Figure 6:
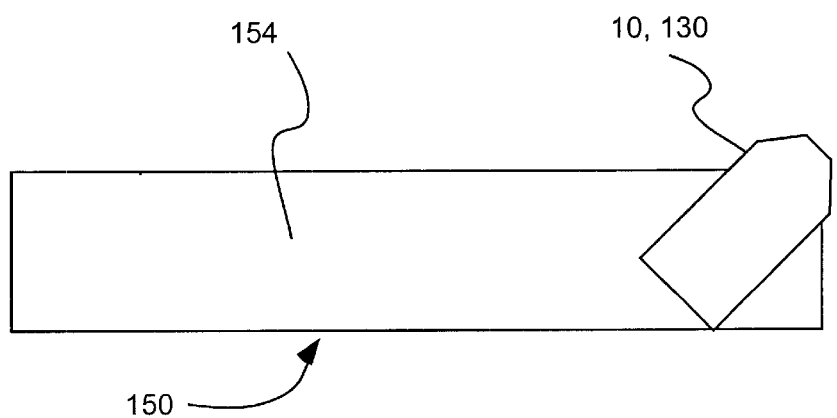
FIG. 6 is a schematic view of a mobile, miniature x-ray source with an integral power source in accordance with an embodiment of the present invention.

The x-ray head can be connected to the high voltage power supply by flexible electrical cables to make it easy to maneuver the head, and to allow the head to fit into long, narrow spaces. An alternative is to build the head as an integral part of the power supply, making a single unit with no exposed cables. The head/power supply combination may be small enough for spaces of moderate size. Referring to FIG. 6, an integral x-ray unit 150 can include an x-ray source 10 or 130 embedded in a power supply 154 to provide a single unit, rather than a head connected by wires to a power supply. The power supply 154 can be electrically coupled to a battery.

To prolong the life of the tube, the following sequence is followed when turning the tube on:
1) a high voltage bias is applied; and
2) a filament current is ramped up over at least several milliseconds so the cathode structure does not receive a thermal shock.

A synergy is developed by the components of the present invention to provide improved performance. For example, typical transmission type tubes with thermionic emitters can have unacceptable window heating and serious voltage instabilities. The x-ray tube of the present invention, however, is stable and cool because of the interaction of the following features:
1) The conical end of the tube and the close proximity of the source of x-rays to the sample allow the tube to function at very low x-ray fluxes.
2) The anode window is thin, but with high thermal conductivity, and the window is sufficiently cooled by ambient air, thus avoiding the necessity of liquid cooling, forced air, fins on the tube exterior, etc.
3) Because the X-ray flux can be small, the cathode can be small, rugged, and it can be operated at an unusually low temperature so that its lifetime is significantly extended.
4) The typical fluctuations in the resistivity of transmission type tubes is compensated by using feedback from the emission current to adjust the filament current, thus providing a level of stability that is more than adequate.

The power supply should match the electron emitter in addition to proving a high DC bias voltage. For example, a thermionic emitter requires an electrical current to heat the filament. The field emitter needs 60 to 80 volts for electron extraction, and a ferroelectric source requires high voltage pulses.

Although ferroelectric electron emitters show promise, they are somewhat expensive and can be less reliable for mobile applications. A thermionic emitter has certain advantages such as immunity to background gas of pressure up to about $10^{-5}$ mm Hg.

Thermionic emitters, however, require a power supply for the filament current, generate heat by the filament, and life of the filament is limited if operated at high temperature to increase electron emission. The lifetime in hours can be estimated well by $t=32/\rho_0$ where $\rho_0$ is the temperature-limited current density. In addition, filaments are extended sources, whereas the ideal electron source is a point source (or at least a very small source). Filament wire is typically bent into a "V" (the hairpin filament). Although this decreases the size of the emitting spot, it creates other problems. The stresses in the bend create hot spots near it, and filament metal evaporates more rapidly in these areas. The resistance of the filament rises, and the heater current will decrease correspondingly if the power supply maintains constant voltage. If the power supply is of the constant current variety, the thin spots in the filament become increasingly hotter and rapidly thinner, resulting in imminent failure. However, if the generator impedance (including the leads) is one third that of the wire, the filament will maintain the same temperature throughout its life.

As an alternative, one could use field emitters in place of a thermionic emitter. Although field emitters generate virtually no heat, they require the maintenance of substantially harder vacuum. Even then, they tend to become dull and inefficient due to erosion of the emitting surface by ions generated by the bombardment of residual gasses by the electron beam. All of the electron emitter types have limited lives, and the emitters are usually the cause of tube failure. Improvements are needed for the production of practical mobile X-ray tubes.

Possibly for thermionic emitters, and certainly for field emitters, a getter is needed to clean up the tube vacuum. Getters are typically metallic and they will distort the electric fields in the tube unless they are placed in a field-free region.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A mobile, miniature x-ray source device, comprising:
   a) an evacuated tube having a length less than approximately 3 inches, and a diameter or width less than approximately 1 inch;
   b) an anode, disposed in the tube, including a material configured to produce x-rays in response to impact of electrons; and
   c) a cathode, disposed in the tube opposing the anode, including a low-power consumption cathode element configured to produce electrons accelerated towards the anode in response to an electric field between the anode and the cathode, the cathode element having a low power consumption less than approximately 1 watt; and
   d) a battery power source, electrically coupled to the anode, the cathode, and the cathode element, to provide power for the cathode element, and to provide the electric field between the anode and the cathode.

2. A device in accordance with claim 1, wherein the battery power source includes a battery operated, high voltage power supply and provides an electric field between the anode and the cathode of at least approximately 15 kilo-volts.

3. A device in accordance with claim 1, further comprising a window, disposed in the evacuated tube at the anode, including a target material configured to produce x-rays in response to impact of electrons.

4. A device in accordance with claim 1, further comprising:
   a field-free region, positioned at the anode, configured to resist positive ion acceleration back towards the cathode element.

5. A device in accordance with claim 4, wherein the electrons impact the anode and heat the anode, releasing residual gas molecules, and wherein the electrons ionize the residual gas molecules to positive ions, which ions would normally be accelerated back to the cathode and sputter-erode the cathode element.

6. A device in accordance with claim 4, further comprising:
   a) an anode tube, disposed at the anode between the anode and the cathode, and electrically coupled to the anode so that the anode and the grounded anode tube have the same electrical potential, the anode tube creating the field-free region.

7. A device in accordance with claim 1, wherein the anode tube and the anode include the same material.

8. A device in accordance with claim 1, further comprising:
   a) a cathode optic, disposed proximate the cathode element, including a plate with an aperture therein configured to allow electrons to pass through the aperture towards the anode; and
   b) an anode optic, disposed proximate the anode, including an anode tube with a hollow aligned to allow electrons to pass through the hollow towards the anode, the anode tube creating the field-free region within the hollow configured to resist positive ion acceleration back towards the cathode element.

9. A device in accordance with claim 1, wherein the cathode element includes a low-mass filament having a mass less than approximately 100 micrograms.

10. A device in accordance with claim 1, further comprising a window, disposed in an end of the evacuated tube, configured to release x-rays, the window being aligned with a longitudinal axis of the evacuated tube configured to release x-rays substantially along the longitudinal axis.

11. A device in accordance with claim 1, further comprising a window, disposed in a side of the evacuated tube, configured to release x-rays transverse to the longitudinal axis.

12. A device in accordance with claim 1, wherein the cathode element includes an electron emitting source selected from the group consisting of: a thermionic emitter, a tungsten filament, a tungsten filament coated with mixed oxides of alkaline earths, a field emitter, a ferroelectric cathode, a metal tip array, a gated-modulated emitter in an array, a gate-modulated emitter in a field emitting surface, a carbon nanotube, a carbon nanotube with a modulating gate, and heated lanthanum hexaboride.

13. An x-ray source device, comprising:
   a) an evacuated tube;
   b) an anode, disposed in the tube, including a material configured to produce x-rays in response to impact of electrons; and
   c) a cathode, disposed in the tube opposing the anode, including a cathode element configured to produce electrons accelerated towards the anode in response to an electric field between the anode and the cathode; and
   d) a field-free region, positioned at the anode, configured to resist positive ion acceleration back towards the cathode element.

14. A device in accordance with claim 13, wherein the electrons impact the anode and heat the anode, releasing residual gas molecules, and wherein the electrons ionize the residual gas molecules to positive ions, which ions would normally be accelerated back to the cathode and sputter-erode the cathode element.

15. A device in accordance with claim 13, further comprising:
   a) an anode tube, disposed at the anode between the anode and the cathode, and electrically coupled to the anode so that the anode and the anode tube have the same electrical potential, the anode tube creating the field-free region.

16. A device in accordance with claim 15, wherein the anode tube and the anode include the same material.

17. A device in accordance with claim 13, wherein the evacuated tube has a length less than approximately 3 inches, and a diameter or width less than approximately 1 inch; wherein the cathode element has a low power consumption less than approximately 1 watt; and further comprising:
   a battery power source, electrically coupled to the anode, the cathode, and the cathode element, to provide power for the cathode element, and to provide the electric field between the anode and the cathode.

18. A device in accordance with claim 13, further comprising:
   a) a cathode optic, disposed proximate the cathode element, including a plate with an aperture therein configured to allow electrons to pass through the aperture towards the anode; and
   b) an anode optic, disposed proximate the anode, including an anode tube with a hollow aligned to allow electrons to pass through the hollow towards the anode, the anode tube creating the field-free region within the hollow.

19. A device in accordance with claim 13, wherein the cathode element includes a low-mass filament having a mass less than approximately 100 micrograms.

20. A device in accordance with claim 13, wherein the cathode element includes an electron emitting source selected from the group consisting of: a thermionic emitter, a tungsten filament, a tungsten filament coated with mixed oxides of alkaline earths, a field emitter, a ferroelectric cathode, a metal tip array, a gated-modulated emitter in an array, a gate-modulated emitter in a field emitting surface, a carbon nanotube, a carbon nanotube with a modulating gate, and heated lanthanum hexaboride.

21. An x-ray source device, comprising:
   a) an evacuated tube having first and second ends;
   b) an anode, disposed at the first end of the tube;
   c) a window, disposed at the first end of the tube, including a material configured to produce x-rays in response to impact of electrons;
   d) a cathode, disposed at the second end of the tube opposing the anode;
   e) an electron emitter, disposed at the second end of the tube, configured to produce electrons accelerated towards the anode in response to an electric field between the anode and the cathode;
   f) a cathode optic, disposed proximate the electron emitter, including a plate with an aperture therein configured to allow electrons to pass through the aperture towards the anode; and
   g) an anode optic, disposed proximate the anode, including an anode tube with a hollow aligned to allow electrons to pass through the hollow towards the anode, the anode tube creating a field-free region within the hollow configured to resist positive ion acceleration back towards the cathode element.

22. A device in accordance with claim 21, wherein the anode tube of the anode optic is directly attached to the target material.

23. A device in accordance with claim 21, wherein the anode tube and the anode are formed of the same material.

24. A device in accordance with claim 21, further comprising:
   a) a shield surrounding at least a portion of the evacuated tube; and
   b) an insulating material disposed between the evacuated tube and the shield.

25. A device in accordance with claim 21, further comprising:
   a) an x-ray filter, disposed at the output window adjacent the target material; and
   b) an x-ray collimator, disposed at the output window, including an aperture to configured to allow x-rays therethrough in a desired direction.

26. A device in accordance with claim 21, wherein the electrons impact the anode and heat the anode, releasing residual gas molecules, and wherein the electrons ionize the residual gas molecules to positive ions, which positive ions would normally be accelerated back to the electron emitter.

27. A device in accordance with claim 21, wherein the cathode element includes a low-mass filament having a mass less than approximately 100 micrograms.

28. A device in accordance with claim 21, wherein the electron emitter is selected from the group consisting of: a thermionic emitter, a tungsten filament, a tungsten filament coated with mixed oxides of alkaline earths, a field emitter, a ferroelectric cathode, a metal tip array, a gated-modulated emitter in an array, a gate-modulated emitter in a field emitting surface, a carbon nanotube, a carbon nanotube with a modulating gate, and heated lanthanum hexaboride.

* * * * *